(12) United States Patent
Fischer et al.

(10) Patent No.: US 8,790,353 B2
(45) Date of Patent: Jul. 29, 2014

(54) DEVICE FOR MECHANICAL LITHOTRIPSY AND REMOVAL OF CALCULI THAT FORM IN THE BILE DUCT OR IN THE URINARY SYSTEM

(75) Inventors: Gerald Fischer, Hoechstadt (DE); Martin Bayer, Roedental (DE)

(73) Assignee: Medwork Medical Products and Services GmbH, Hoechstadt/Aisch (DE)

( * ) Notice: Subject to any disclaimer, the term of this patent is extended or adjusted under 35 U.S.C. 154(b) by 573 days.

(21) Appl. No.: 12/949,582

(22) Filed: Nov. 18, 2010

(65) Prior Publication Data

US 2011/0118746 A1    May 19, 2011

Related U.S. Application Data

(60) Provisional application No. 61/262,698, filed on Nov. 19, 2009.

(51) Int. Cl.
*A61B 17/221* (2006.01)
*A61B 17/29* (2006.01)
*A61B 17/00* (2006.01)

(52) U.S. Cl.
CPC ....... *A61B 17/221* (2013.01); *A61B 2017/2903* (2013.01); *A61B 2017/2212* (2013.01); *A61B 2017/00367* (2013.01); *A61B 2017/2923* (2013.01)
USPC .......................................... 606/128; 606/113

(58) Field of Classification Search
CPC ............ A61N 2017/00367; A61N 2017/2903; A61N 17/221
USPC ................................... 606/113, 114, 127, 128
See application file for complete search history.

(56) References Cited

U.S. PATENT DOCUMENTS

| | | | | |
|---|---|---|---|---|
| 4,691,705 A | * | 9/1987 | Okada | 606/127 |
| 5,722,980 A | * | 3/1998 | Schulz et al. | 606/128 |
| 5,788,710 A | * | 8/1998 | Bates et al. | 606/127 |
| 2003/0109889 A1 | * | 6/2003 | Mercereau et al. | 606/127 |
| 2004/0260246 A1 | * | 12/2004 | Desmond | 604/174 |

FOREIGN PATENT DOCUMENTS

| | | |
|---|---|---|
| DE | 3216178 | 11/1983 |
| DE | 3316260 | 11/1984 |
| DE | 8706587 | 10/1987 |

OTHER PUBLICATIONS

German Search Report.

* cited by examiner

*Primary Examiner* — Thomas McEvoy
*Assistant Examiner* — Julie A Szpira
(74) *Attorney, Agent, or Firm* — Lucas & Mercanti, LLP

(57) ABSTRACT

The device for mechanical lithotripsy and removal of stones that form in the bile duct or urinary system has a stone collection basket at a distal end of a tube and two actuators at the proximal end of the tube. A cable runs through the tube and connects each actuator to the basket. The actuators are screw drives and form a common structural unit that is concentric to the tube and the cable. One actuator controls the opening and closing of the basket while the other actuator controls the force transmitted through the cable to the basket to allow for crushing of the stone in the basket.

18 Claims, 2 Drawing Sheets

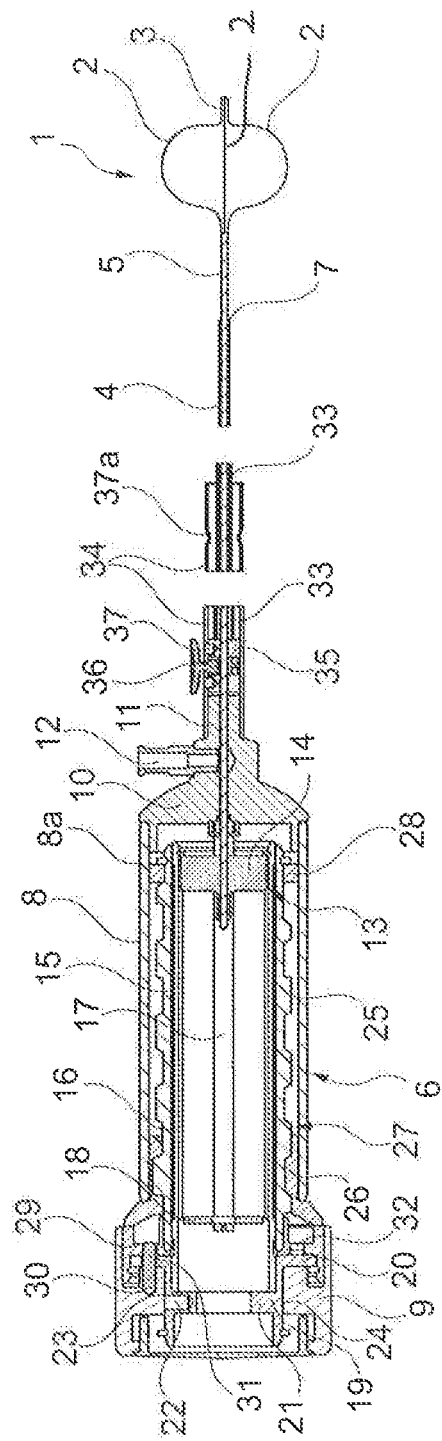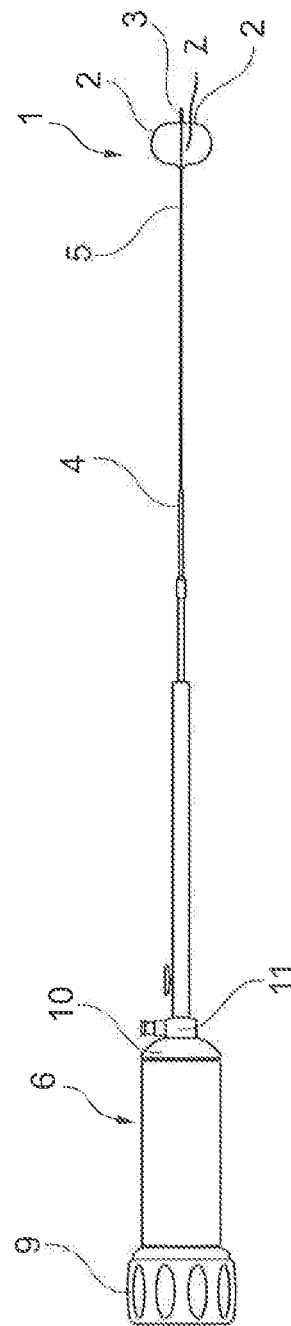

DEVICE FOR MECHANICAL LITHOTRIPSY AND REMOVAL OF CALCULI THAT FORM IN THE BILE DUCT OR IN THE URINARY SYSTEM

This application is a conventional application of provisional application No. 61/262,698 filed Nov. 19, 2009, the priority is of which hereby claimed and which is incorporated by reference herein.

FIELD OF THE INVENTION

The invention concerns a device for mechanical lithotripsy and removal of calculi that form in the bile duct or in the urinary system, for use in connection with an endoscopic retrograde cholangiopancreatography and comprising a stone collecting basket arranged on a distal end of the device, a cable connected to said stone collecting basket and guided in a tube for initiating an opening or closing movement of said stone collecting basket for receiving the calculus and for introducing a force form lithotripsy thereof, and further comprising an actuation device arranged on a proximal end both of the tube and the cable, said actuation device comprising a second actuating element for initiating the opening or closing movement of the stone collecting basket, and a first actuating element configured as a screw drive being provided for the lithotripsy of the calculus.

Devices of the pre-cited type are used for removing stones out of a bile and pancreatic duct, a kidney, a urinary bladder or a ureter in a natural manner, i.e. without surgery. The stone collecting basket arranged on the distal end of the device is moved in most cases through a guide wire guided in a separate lumen up to the stone situated in the bile duct or in another organ. The stone collecting basket pushed out of the tube by the cable then opens due to its elastic pre-stress and attains its largest radial dimension. The stone collecting basket is now moved up to the calculus till it comes to be situated in the interior of the basket, i.e. between the basket wires. Upon a subsequent pulling movement of the cable relative to the tube, the stone collecting basket contracts firmly around the stone, so that it can be made to pass, with the help of the cable and the tube, through the corresponding body openings and be reliably removed. However, considerable problems arise if the dimensions of the calculus are such that it cannot be pulled through body openings like, for example, the bile duct or the ureter. A forced extraction of the calculus would lead to severe wounding of the patient to be treated.

In addition to the equipment for capturing and removing the stone, therefore, a variety of solutions have been proposed by the prior art for crushing too large stones into pieces for enabling it to pass through the corresponding body openings. The lithotripters used for this purpose can be generally classified as those that crush the stone situated in the body of the patient by ultrasonic means and those using mechanical means. The present invention concerns a mechanical lithotripter.

A device of the pre-cited type for mechanical lithotripsy and removal of calculi that form in the bile duct or in the urinary system is disclosed in DE 32 16 178 A1. This device consists of an extractor and a device for lithotripsy that can be combined with this. The extractor comprises an actuating element with a thrust rod telescoped in a bushing, the cable leading to the stone collecting basket being fixed on the thrust rod, which comprises a handle, and the tube being fixed on the bushing. Thus, an axial displacement of the thrust rod in the bushing leads to an opening or a closing of the stone collecting basket depending on the direction of movement, so that, for instance, a stone in the bile duct is captured by the stone collecting basket and can be removed out of the body of the patient by moving the entire device in proximal direction. In addition to this extractor, the prior art provides a separate lithotripter which is fixed if necessary on the actuating element. The actuating element is a spindle drive with retainers extending radially thereto which, after the attachment of the lithotripter, are applied on one side to the handle of the first actuating element and on the other side to a head piece connected to the bushing. If it is determined that the calculus is of a size that prevents its problem-free removal, such a strong tractive force is applied to the cable through the lithotripter attached to the actuating element, that the stone situated in the stone collecting basket is crushed into several small particles. These particles can then be removed with the stone collecting basket.

SUMMARY OF THE INVENTION

The object of the invention is to provide an actuation device for the generic device, which actuation device is easy to handle and suitable both for the precise positioning and for opening and closing the stone collecting basket during capturing of the stone as also for a lithotripsy and subsequent extraction of the calculus.

The invention achieves the above object by the fact that the second actuating element is likewise configured as a screw drive and that both actuating elements form a common structural unit that is arranged substantially concentrically to the tube and the cable, and the second actuating element can be optionally coupled through a switching device to a turning handle extending likewise substantially concentrically to the cable and the tube. The important advantages of the inventive configuration of the actuation device consist in that with the help of the second actuating element configured as a screw drive, it is possible to execute very precise actuating movements, also at a relatively high speed. Advantageously, the two actuating elements are combined into one common structural unit and the thus created actuation device, due to its concentric arrangement relative to the tube and the cable can dispense with additional transmission elements. Through the switching device, the operator of the device can exert an enhanced tractive force on the cable immediately after the stone has been captured.

The problematic abatement of the tractive force following capturing of the stone experienced with known devices according to the generic prior art can possibly result in a re-opening of the stone collecting basket to an extent that it loses the stone. This happens when the first actuating element serving as a lithotripter is mounted on the second actuating element. Moreover, the second actuating element in the prior art device can be operated only through relatively imprecise axial actuating movements because it is a slide acting directly on the cable.

In a further development of the invention, the second actuating element comprises a screw drive with a large thread pitch and the first actuating element comprises a screw drive with a very small thread pitch. Due to the large thread pitch of its screw drive, the second actuating element can transmit not only a precisely dosed but also a very fast actuating movement to the stone collecting basket, so that, at the very moment that the basket surrounds the stone in its open state, it grips the stone through a very fast closing and twisting movement. In contrast with the first actuating element, it is intended to apply a very high force to the cable which is then transmitted to the stone collecting basket and leads to a controlled crushing of the stone. The force required for this is reduced to a minimum by the fact that the first actuating element possesses a screw drive with a very small pitch.

Moreover, the first actuating element comprises a bush-type nut with an inner thread, which nut cooperates with a spindle which, in turn, is connected to the cable. This screw drive formed by the bush-type nut and the spindle possesses a very small pitch, so that when the bush-type nut is turned relative to the spindle by means of the turning handle coupled to thereto, a very small actuating movement between the cable and the tube is caused which, in its turn, leads to an increase of the tension between the stone and the basket wires surrounding the stone. The coaxial arrangement of these two components relative to the cable and the tube results in the fact that no additional transmission elements are required between this drive and the cable or the tube, because all movements have one common central longitudinal axis.

The spindle must be safe against rotation relative to an outer housing of the actuation device but must be guided for longitudinal movement. This anti-rotation feature can be realized by the fact that the outer housing comprises a cylinder and a head piece closing this cylinder at a front end, whereby at least one guide pin projects from the head piece and engages the spindle as an anti-rotation feature of the spindle. This at least one guide pin can project through bores in the spindle and be fixed at the other end in a guide disk. Thus, the guide pin which is unmovable relative to the housing, starts from the head piece of the outer housing and is fixed at its other end in the guide disk that is guided for rotation relative to the bush-type nut. The guide disk can be fixed for rotating in a circumferential groove arranged in the inner peripheral surface of the bush-type nut. Further, the bush-type nut, in turn, is guided for rotation relative to the outer housing and its head piece.

When the device is used for the lithotripsy of a stone clamped in the stone collecting basket, the operator of the device therefore grasps the outer housing on its outer periphery with one hand and turns the turning handle with his other hand, so that the bush-type nut is turned both relative to the spindle and to the firmly held outer housing.

The transmission of the turning movement of the turning handle is further effected by the fact that it is arranged on a section of the outer peripheral surface of the bush-type nut and this nut comprises a radially outwards pointing flange, whereby entraining elements extending in axial direction from the turning handle project into openings of the nut. However, the component carrying the turning handle and comprising the flange can also be configured as a separately manufactured piece of pipe that is firmly connected to the bush-type nut by shrink fitting.

The entraining elements may be configured in the form of claws or cylindrical pins, so that, when the turning handle is turned, they apply a torque to the bush-type nut through positive engagement with the outwards pointing flange. According to a further feature of the invention, a further bushing is arranged on a section of an outer peripheral surface of the bush-type nut and, together with a second nut fixedly arranged in an outer housing of the actuation device, forms the second actuating element for the opening and closing movement of the stone collecting basket. By means of this actuating element which must be configured with a large thread pitch between the bushing and the second nut, a fast actuating movement is executed during the opening and closing of the stone collecting basket.

The bushing likewise comprises a radially outward pointing flange which is arranged parallel and next to the flange of the second nut and comprises openings extending in axial direction. Upon an axial movement of the turning handle in direction of the flange of the nut, the entraining elements couple the two flanges to each other and to the turning handle by positive engagement. When the turning handle takes this end position in distal direction, its turning movements are transmitted both to the bush-type nut and the second nut.

Moreover, a spring-biased detent element which cooperates with a locking contour provided on an inner peripheral surface of a hub of the turning handle is arranged in the section of the bush-type nut on which the turning handle is disposed. Accordingly, the turning handle can be moved axially into two different positions and is retained in the respective position through the spring-biased element cooperating with the locking contour.

According to an advantageous feature of the invention, the tube is made of a soft plastic and partially surrounded by a flexible metal hose. During the lithotripsy of the stone, the distal end of this flexible hose bears against the proximal end of the stone collecting basket, so that a stable support of the stone collecting basket is obtained during the crushing of the stone. Due to its low rigidity, the tube made of a soft plastic would not be suitable for providing such a stable support of the stone collecting basket during the crushing of the stone. Advantageously, the metal hose can have a helical structure so as to be flexible on a whole.

Further, the metal hose must be displaceable relative to the tube with the help of an adjusting element, so that, when the device is introduced into the bile duct of the patient, at first only the soft plastic comes into contact with the wall of the bile duct or the wall of other organs. It is only at the beginning of the lithotripsy that the metal hose is pushed so far in distal direction of the device with the help of the adjusting element that it bears through its distal end against the stone collecting basket. In this position, the metal hose can provide an adequate support of the stone collecting basket during the lithotripsy.

An adjusting element serving for the axial displacement of the metal hose can be realized advantageously in that the metal hose is telescopically guided in a sliding pipe firmly connected to the outer housing. Moreover, means are provided that engage radially through the sliding pipe and are fixed to the metal hose, so that the components metal hose and sliding pipe are displaceable relative to each other. Corresponding means are realized, inter alia, in that the sliding pipe comprises over almost its entire length an oblong hole comprising locking apertures on both ends, that the metal hose comprises on its proximal end a slide guided in the interior of the sliding pipe and that a locking element for cooperating with a respective one of the locking apertures is arranged on the slide. However, the locking apertures can be a plurality of locking apertures, preferably five in number, the locking element being displaceable into anyone of the locking apertures. Moreover, it is also possible to immobilize the metal hose that is infinitely adjustable relative to the sliding pipe, in any position on the sliding pipe, for which purpose, a force-locking clamping device must be provided between said components.

Further, the locking element comprises a pushbutton which is resilient in radially outward direction and whose manual actuation in a direction opposed to the spring causes the locking element to be moved out of the locking aperture. Following this, the metal hose can be displaced so far relative to the sliding pipe that the locking element snaps into the next locking aperture.

Finally, it is possible to arrange a connecting nipple on the head piece configured together with the outer housing, through which nipple a contrast liquid can be introduced into the lumen. This contrast liquid flows through the lumen in which the cable is lodged into the region of the calculus. Such contrast liquids are used to make the stone more conspicuous in radiological images.

The entire equipment can advantageously be put together by combining components that can be economically manufactured. Some of these components, such as, for example, the first nut, the bushing and the outer housing can be made out of light metal by shaping without chip removal.

BRIEF DESCRIPTION OF THE DRAWING

Further features of the invention will result from the following description and appended drawing in which one example of embodiment of the invention is shown in simplified illustrations. The figures show:

FIG. 1, a longitudinal section through a device of the invention for mechanical lithotripsy, showing an actuation device, a fractional piece of a sliding pipe and a distal end section, FIG. 2, an overall view of a device of the invention, represented on a smaller scale than in FIG. 1, FIG. 3, a longitudinal section through an actuation device configured according to FIG. 1, showing its actuating elements in a position in which a stone collecting basket, not shown, is situated in a retracted position in a lumen of a tube, and FIG. 4, a top view of a sliding pipe.

DETAILED DESCRIPTION OF THE DRAWING

Figure 3:
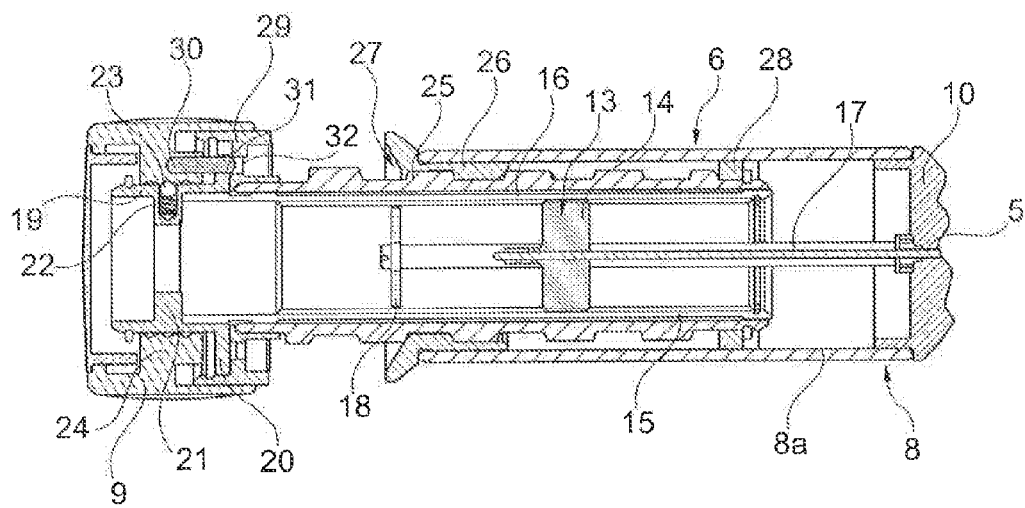

Identified at 1 in FIGS. 1 and 2 is a stone collecting basket which is in its opened position for receiving a calculus. The stone collecting basket 1 comprises at least four basket wires 2 that are combined into a mushroom-shaped guide element 3 at their distal end. A proximal and of the stone collecting basket 1 is engaged by a cable 5 which is guided in a tube 4, and cable 5 and tube 4 are connected at their other ends to an actuation device 6. The cable 5 extends in a lumen 7 of the tube 4 that is made of a soft plastic and extends in distal direction to near the stone collecting basket 1. The basket wires 2 and the distal end of the tube 4 are configured such that, during its inward movement into the lumen 7, during which it contracts, the stone collecting basket 1 executes a turning movement about its longitudinal axis through which the reception of the calculus is considerably improved.

The actuation device 6 comprises an outer housing 8 of a generally cylindrical configuration arranged concentrically both to the cable 5 and the tube 4, said actuation device 6 further comprising, on its proximal end a likewise cylindrical turning handle 9. The structure and function of the actuation device 6 are described in the following, particularly with reference to FIGS. 1 and 3:

The outer housing 8 is closed at one front end by a head piece 10 through which head piece 10, the cable 5 is guided into the interior of the outer housing 8. In addition, this head piece 10 receives and fixes the tube 4 with help of an axial extension 11 configured thereon. A radially extending connecting nipple 12 is inserted into the extension 11, through which nipple 12 a contrast agent can be introduced into the lumen 7 which, functioning as a catheter, routes the contrast agent into the region of the calculus.

The actuation device 6 further comprises a first actuating element 13 configured as a screw drive and made up of a spindle 14 and a bush-type nut 16 comprising an inner thread 15. The proximal end of the cable 5 is fixed centrally in the spindle 14 which possesses an outer thread. To prevent the spindle 14 from rotating together with the bush-type nut 16 relative to the cable 5 and the outer housing 8, the spindle 14 is guided by at least one guide pin 17 on the head piece 10 and at the opposite end, on a guide disk 18. Each of these guide pins 17 extends through and out of a bore, not specifically shown, such that the spindle 14, although secured against rotation, is still guided for longitudinal displacement. A pipe piece 19 comprising a first flange 20 is disposed on the end of the bush-type nut 16 facing the turning handle 9. Besides this, the pipe piece 19 possesses an inwards protruding collar 21 in which at least one spring-biased detent element 22 is arranged. This detent element 22 cooperates with a locking contour 23 that is configured on an inner peripheral surface of a hub 24 of the turning handle 9. The locking contour 23 can be realized by configuring grooves, cavities or projections on the periphery of the pipe piece 19.

Further, the bush-type nut 16 is surrounded by a bushing 25 which, together with a second nut 26 arranged in the outer housing 8, forms a second actuating element 27. The second nut 26 is connected firmly to the outer housing 8, while the bushing 25 is arranged for rotating freely on the bush-type nut 16. In addition, the bushing 25 is surrounded at its distal end by a sliding ring 28 through which it slides in the interior of the cylindrical outer housing 8. On its proximal end, the bushing 25 comprises a flange element 29 which protrudes radially outwards and extends parallel to the first flange 20 while being situated directly next to this flange 20.

The turning handle 9 possesses entraining elements 30 which extend in axial direction into a through-aperture 31 of the first flange 20 and can be displaced so far by an axial movement of the turning handle 9 that they project out of the through-apertures 31 to engage into openings 32 of the flange element 29. The entraining elements 30 take this position, for example in FIG. 1, while in FIG. 3, they mesh only with the first flange 20, so that the flange element 29 and, thus also, the bushing 25 are not turned by the turning handle 9.

As can be seen further in FIG. 1 in combination with FIG. 2, the tube 4 is surrounded by a metal hose 33. During introduction of the tube 4 with retracted stone collecting basket 1, for example, into the bile duct, the tube 4 made, as already mentioned, of a soft plastic, protrudes with a certain length beyond the metal hose 33. Because the tube 4 is very soft and very elastic, wounds in the hollow spaces of the organs through which the tube 4 is pushed are avoided.

The metal hose 33, in turn, is surrounded in its end region facing the actuation device 6 by a sliding pipe 34 which is fixed in place on the axial extension 11 of the head piece 10. Further, a slide 35 is firmly connected to the metal hose 33, the outer dimensions of the slide 35 being matched to the inner dimensions of the sliding pipe 34. In addition, a locking element 36 is a component part of the slide 35. This locking element 36 starts from the slide 35 and projects in radial direction into a locking aperture 37 of the sliding pipe 34.

Figure 4:
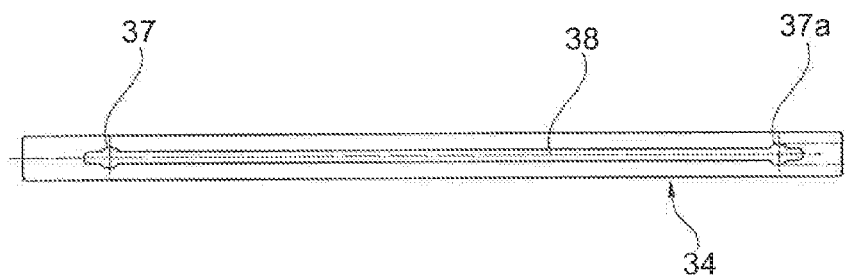

As disclosed in FIG. 4, the sliding pipe 34 comprises two spaced apart locking apertures 37 and 37a that are connected to each other through an oblong hole 38. If the locking element 36 which is configured as a resilient pushbutton is actuated in the position shown in FIGS. 1 and 2, the slide 35 can be displaced relative to the sliding pipe 34 in distal direction so far that the locking element 36 penetrates into the locking aperture 37a situated on the distal end of the sliding pipe 34. As a result, the metal hose 33 is displaced in distal direction via the slide 35 through the distance between the two locking apertures 37 and 37a. In this position, a distal end of the metal hose 33 is situated in the region of the stone collecting basket 1, so that this can be supported on the end of the metal hose 33 during a lithotripsy.

The function of the device represented in FIGS. 1 to 4 is as follows:

In FIGS. 1 and 2, the device is represented with opened stone collecting basket 1. If, in the position of its entraining element 30 illustrated in FIG. 1, the turning handle 9 is turned in anti-clockwise direction, the bushing 25 is screwed so far out of the second nut 26 that the stone collecting basket 1 comes to be situated within the tube 4. In this state, the tube 4 is introduced into the body of the patient up to the region of the calculus. When the tube 4 takes a position directly next to the calculus, the bushing 25 is screwed so far into the interior of the outer housing 8 by turning the turning handle 9 that the stone collecting basket 1 opens. When it takes a position in which the calculus can be captured, the turning handle 9 is turned again in anti-clockwise direction so that the stone collecting basket 1 executes a closing movement during which it twists and thus captures the calculus. When the calculus is situated within the stone collecting basket 1 and the problem exists that this cannot be transported through the bile duct and through the alimentary tract, the stone has to be crushed.

For this purpose, at first, the metal hose 33 is pushed by means of the locking element 36 and the slide 35 so far in the sliding pipe 34 till the locking element 36 locks into the locking aperture 37a on the distal and of the sliding pipe 34. The distal end of the metal hose 33 now bears against the stone collecting basket 1.

Following this, the turning handle 9 is displaced so far in axial direction that the entraining elements 30 projecting from the handle are pulled out of the openings 32 and thus mesh now only with the through-apertures 31. A turning of the turning handle 9 relative to the outer housing in anti-clockwise direction results in that the bush-type nut 16 is turned in the corresponding direction of rotation and that the spindle 14 is moved in direction of the proximal and of the actuation device 6 through the small-pitch meshing threads of the bush-type nut 16 and the spindle 14. Because the stone collecting basket 1 is supported on the end of the metal hose 33, the forces transmitted by the cable 5 to the stone collecting basket 1 act in radial direction on the calculus and lead to its destruction. Following this, the components of the calculus can be extracted together with the stone collecting basket 1 when the device is taken out of the bile duct. In order to always guarantee that the device can be removed from the bile duct in case the stone cannot be crushed in this manner, the stone collecting basket 1 can comprise at least one predetermined breaking point which leads to an opening of the stone collecting basket 1 and thus to a releasing of the stone when a maximum force is exceeded.

The device of the invention thus possesses an actuation device which, although comprising only a small number of components, enables a very precise capturing of the calculus and its subsequent crushing as also the extraction of the parts of the calculus.

LIST OF REFERENCE NUMERALS

1 Stone collecting basket
2 Basket wires
3 Guide element
4 Tube
5 Cable
6 Actuation device
7 Lumen
8 Outer housing
8a Cylinder
9 Turning handle
10 Head piece
11 Axial extension
12 Connecting nipple
13 First actuating element
14 Spindle
15 Inner thread
16 Bush-type nut
17 Guide pin
18 Guide disk
19 Pipe piece
20 Flange
21 Collar
22 Detent element
23 Locking contour
24 Hub
25 Bushing
26 Second nut
27 Second actuating element
28 Sliding ring
29 Flange element
30 Entraining element
31 Through-aperture
32 Opening
33 Metal hose
34 Sliding pipe
35 Slide
36 Locking element
37 Locking aperture
37a Second locking aperture
38 Oblong hole

The invention claimed is:

1. A device for mechanical lithotripsy and removal of calculi that form in
the be duct or in the urinary system, for use in connection with an endoscopic retrograde cholangiopancreatography, the device comprising:
a stone collecting basket arranged on a distal end of the device,
a cable connected to said stone collecting basket and guided in a tube for initiating an opening or closing movement of said stone collecting basket for receiving the calculus,
an actuation device arranged on a proximal end of both the tube and the cable, said actuation device comprising
a first actuating element configured as a screw drive, the first actuating element for the lithotripsy of the calculus,
a second actuating element configured as a screw drive, the second actuating element for an opening and a dosing movement of the stone collecting basket,
the first actuating element and the second actuating element forming a common structural unit that is arranged substantially concentrically to the tube and the cable,
a turning handle coupled to a switching device, the turning handle substantially concentrically to the cable and the tube, the turning handle having a first position for the lithotripsy of the calculus and a second position for the opening and the closing movement of the stone collecting basket, and
the switching device having a first position where the switching device is coupled to the first actuating element for the lithotripsy of the calculus and a second position where the switching device is coupled to the second actuating element for the opening and the closing movement of the stone collecting basket.

2. The device according to claim 1, wherein the second actuating element comprises a screw drive with a second thread pitch and the first actuating element comprises a screw drive with a first thread pitch, the first thread pitch is smaller than the second thread pitch.

3. The device according to claim 1, wherein the first actuating element comprises a bush-type nut comprising an inner thread, which nut cooperates with a spindle which is connected to the cable.

4. The device according to claim 3, wherein the spindle is prevented from rotation relative to an outer housing of the actuation device but is guided for longitudinal movement.

5. The device according to claim 4, wherein the outer housing comprises a cylinder and a head piece closing the cylinder at a front end, and at least one guide pin projects from the head piece and engages the spindle to prevent rotation of the spindle relative to the outer housing.

6. The device according to claim 5, wherein the at least one guide pin projects through bores in the spindle and is fixed at another end of the cylinder, in a guide disk.

7. The device according to claim 3, wherein the turning handle is arranged on a section of the outer peripheral surface of the bush-type nut, said section of the nut comprises a radially outwards pointing flange, and entraining elements extending in axial direction from the turning handle project into openings of the nut.

8. The device according to claim 3, wherein a bushing is arranged on a section of an outer peripheral surface of the bush-type nut and forms, together with a second nut which is fixedly arranged in an outer housing of the actuation device, the second actuating element.

9. The device according to claim 6, wherein the first actuating element comprises a bush-type nut comprising an inner thread, which nut cooperates with a spindle which is connected to the cable, the turning handle is arranged on a section of the outer peripheral surface of the nut, the first nut comprises a radially outwards pointing flange, and entraining elements extending in axial direction from the turning handle project into through-apertures in the flange of the nut, the bushing comprises a radially outward pointing flange element which is arranged parallel and next to the flange of the nut and comprises openings extending in axial direction, and, upon an axial movement of the turning handle in direction of the flange element, the entraining elements couple the flange element and the flange to each other by positive engagement.

10. The device according to claim 7, wherein a spring-biased detent element is arranged in the section of the nut on which the turning handle is arranged, which detent element cooperates with a locking contour configured on an inner peripheral surface of a hub of the turning handle.

11. The device according to claim 1, wherein the tube is made of a soft plastic and partially surrounded by a flexible metal hose.

12. The device according to claim 11, wherein the flexible metal hose comprises an outer peripheral wall comprising helical windings.

13. The device according to claim 11, wherein the metal hose can be displaced on the tube by an adjusting element, such that a distal end of the metal hose bears against the stone collecting basket.

14. The device according to claim 11, wherein the outer housing of the actuation device comprises a cylinder and a head piece which closes this cylinder at a front end, the metal hose is displaceable by an adjusting element on the tube, such that a distal end of the metal hose bears against the stone collecting basket and that the adjusting element is constituted by a telescopic arrangement of the metal hose in a sliding pipe which is connected to the outer housing.

15. The device according to claim 14, wherein the sliding pipe comprises over almost an entire length thereof, an oblong hole comprising locking apertures on both ends, the metal hose comprises on its proximal end, a slide guided in the interior of the sliding pipe and that a locking element cooperating with a respective one of the locking apertures is arranged on the slide.

16. The device according to claim 15, wherein the locking element is configured as a radially outwards resilient push-button.

17. The device according to claim 1, wherein the outer housing of the actuation device comprises a cylinder and a head piece which closes said cylinder at a front end, a connecting nipple is arranged in the head piece, which nipple, for introducing a contrast liquid into the region of the calculus, opens into a lumen in which the cable is lodged.

18. The device according to claim 8, wherein the bush type nut, the bushing and a cylinder of the outer housing are configured as structural components made without chip removal.

* * * * *